US008548120B2

(12) United States Patent
Shi et al.

(10) Patent No.: US 8,548,120 B2
(45) Date of Patent: *Oct. 1, 2013

(54) DENTAL IMAGING USING SEGMENTATION AND AN ARCH

(71) Applicant: Dental Imaging Technologies Corporation, Hatfield, PA (US)

(72) Inventors: Hongjian Shi, Souderton, PA (US); Arun Singh, North Wales, PA (US); Ed Marandola, Gwynedd, PA (US); Uwe Mundry, Landrum, SC (US); Somchai Kreang-arekul, Nonthaburi (TH)

(73) Assignee: Dental Imaging Technologies Corporation, Hatfield, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/693,854

(22) Filed: Dec. 4, 2012

(65) Prior Publication Data
US 2013/0094748 A1    Apr. 18, 2013

Related U.S. Application Data

(63) Continuation of application No. 12/847,590, filed on Jul. 30, 2010, now Pat. No. 8,325,874.

(60) Provisional application No. 61/230,411, filed on Jul. 31, 2009.

(51) Int. Cl.
*A61B 6/14*     (2006.01)
(52) U.S. Cl.
USPC ............................................. 378/38; 382/131

(58) Field of Classification Search
USPC ............... 378/38–40, 62, 210; 382/128, 131, 382/132
See application file for complete search history.

(56) References Cited

U.S. PATENT DOCUMENTS

| 84,415 | A | 11/1868 | Cuplin |
| 5,214,686 | A | 5/1993 | Webber |
| 5,663,998 | A | 9/1997 | Suzuki et al. |
| 5,912,942 | A | 6/1999 | Schick et al. |
| 5,995,583 | A | 11/1999 | Schick et al. |
| 6,042,267 | A | 3/2000 | Muraki et al. |
| 6,134,298 | A | 10/2000 | Schick et al. |

(Continued)

FOREIGN PATENT DOCUMENTS

| EP | 1973075 | 9/2008 |
| WO | 2004/019783 | 3/2004 |
| WO | 2007/057083 | 5/2007 |
| WO | 2008/087394 | 7/2008 |

OTHER PUBLICATIONS

PCT/US2010/043931 International Search Report and Written Opinion dated Sep. 22, 2010 (11 pages).

(Continued)

*Primary Examiner* — Jurie Yun
(74) *Attorney, Agent, or Firm* — Michael Best & Friedrich LLP

(57) ABSTRACT

A method and a system for generating an image by obtaining x-ray image data, segmenting the x-ray image data into a first portion above a vertical threshold and a second portion below the vertical threshold. Further, the method and the system include generating an arch for the second plurality of slices, and generating an image based on the arch.

18 Claims, 6 Drawing Sheets

(56) References Cited

U.S. PATENT DOCUMENTS

| | | | |
|---|---|---|---|
| 6,152,731 | A | 11/2000 | Jordan et al. |
| 6,385,332 | B1 | 5/2002 | Zahalka et al. |
| 6,404,854 | B1 | 6/2002 | Carroll et al. |
| 6,985,612 | B2 | 1/2006 | Hahn |
| 7,006,600 | B1 | 2/2006 | Krema et al. |
| 7,084,868 | B2 | 8/2006 | Farag et al. |
| 7,090,395 | B2 | 8/2006 | Glazer |
| 7,262,399 | B2 | 8/2007 | Hayashi et al. |
| 7,281,847 | B2 | 10/2007 | Kokkaliaris et al. |
| 7,336,763 | B2 | 2/2008 | Spartiotis et al. |
| 7,388,973 | B2 | 6/2008 | Fidrich et al. |
| 7,397,890 | B2 | 7/2008 | Sukovic et al. |
| 7,421,059 | B2 | 9/2008 | Suzuki et al. |
| 7,453,986 | B1 | 11/2008 | Isaksen |
| 7,480,366 | B2 | 1/2009 | Mazuir |
| 7,505,558 | B2 | 3/2009 | Nanni et al. |
| 7,545,909 | B2 | 6/2009 | Singh et al. |
| 7,615,754 | B2 | 11/2009 | Liu et al. |
| 7,655,918 | B2 | 2/2010 | Liu et al. |
| 7,676,022 | B2 | 3/2010 | Pantsar et al. |
| 7,746,339 | B2 | 6/2010 | Matov et al. |
| 7,755,056 | B2 | 7/2010 | Bell |
| 7,783,093 | B2 | 8/2010 | Singh et al. |
| 8,325,874 | B2 * | 12/2012 | Shi et al. .................. 378/38 |
| 2006/0275740 | A1 * | 12/2006 | Singh et al. ............... 433/215 |
| 2007/0041489 | A1 | 2/2007 | Siltanen et al. |
| 2007/0086560 | A1 | 4/2007 | Kia et al. |
| 2007/0223649 | A1 | 9/2007 | De Godzinsky |
| 2007/0297663 | A1 | 12/2007 | Mundry |
| 2008/0019476 | A1 | 1/2008 | Mirzayan |
| 2008/0118020 | A1 | 5/2008 | Thibault et al. |
| 2008/0118021 | A1 | 5/2008 | Dutta et al. |
| 2008/0118022 | A1 | 5/2008 | Hagiwara |
| 2008/0246768 | A1 * | 10/2008 | Murray et al. ............. 345/427 |
| 2008/0267343 | A1 | 10/2008 | Sukovic et al. |

OTHER PUBLICATIONS

Enciso, Reyes, et al., "3D Visualization of the Craniofacial Patient: Volume Segmentation, Data Integration and Animation", Conferences on Orthodontics Advances in Science and Technology, Monterey, Sep. 2002.

Deling, Mi, et al., "Oral Implant Orientation of 3-D Imaging Based on X-Ray Computed Tomography (CT)", Asian Journal of Information Technology, vol. 6, No. 11, pp. 1143-1147, 2007.

Rueda, Sylvia, et al., "Automatic Segmentation of Jaw Tissues in CT Using Active Appearance Models and Semi-automatic Landmarking", MICCAI 2006, LNCS 4190, pp. 167-174, 2006.

Neumann, Patrick, et al., "An Interaction Model for 3D Cutting in Maxillofacial Surgery Planning", Medical Imaging, 1999.

Heimann, Tobias, et al., A Shape-Guided Deformable Model Evolutionary Algorithm Initialization for 3D Soft Tissue Segmentation, IPMI 2007, LNCS 4584, pp. 1-12, 2007.

Lilja, Mikko, et al., "Automatic Segmentation of the Mandible from Limited-Angle Dental X-Ray Tomography Reconstructions", IEEE, pp. 964-967, ISBI 2007.

Zhang, Yong-De, et al., "Robotic System Approach for Complete Denture Manufacturing", IEEE/ASME Transactions on Mechatronics, vol. 7, No. 3, Sep. 2002.

Kondo, Toshiaki, et al., "Tooth Segmentation of Dental Study Models Using Range Images", IEEE Transactions on Medical Imaging, vol. 23, No. 3, Mar. 2004.

Tohnak, S., et al., "Synthesizing Dental Radiographs for Human Identification", Journal of Dental Research, vol. 86, No. 11, pp. 1057-1062, Research Reports, Biomaterials and Bioengineering, 2007.

Office Action from the United States Patent and Trademark Office for U.S. Appl. No. 12/847,590 dated Jun. 4, 2012 (9 pages).

* cited by examiner

DENTAL IMAGING USING SEGMENTATION AND AN ARCH

RELATED APPLICATIONS

The present patent application is a continuation of U.S. application Ser. No. 12/847,590, filed on Jul. 30, 2010, which claims priority to U.S. Provisional Application No. 61/230,411, filed on Jul. 31, 2009, the content of which is hereby incorporated by reference.

BACKGROUND

The present invention relates to x-ray imaging. More particularly, embodiments of the invention relate to panoramic imaging of the human mouth and similar structures.

X-rays have been used in dentistry to image teeth and parts of the mouth for many years. In general, the process involves generating x-rays and directing the x-rays at the patient's mouth. The x-rays are absorbed and reflected differently by different parts of the mouth (e.g., bone versus tissue). This difference in absorption is used to create an image, such as on film or by using an electronic image sensor. Individual images of specific areas of interest can be generated or, if a wider perspective is desired, a panoramic image can be created. Often, a computer tomography ("CT") system is used to generate a panoramic image. In a typical dental CT system, the patient sits upright, and the x-ray source and detector are mounted on opposite ends of a gantry that rotates about a vertical axis through the middle of the patient's head. In general, a panoramic image of the jaw depicts the jaw as if it were imaged onto a cylindrical sheet with the axis of the sheet upright, and as if the sheet were then unrolled into a flat form.

SUMMARY

Although a number of technologies designed to generate panoramic images of the mouth exist, there are a number of deficiencies with these technologies. For example, since the jaw is not cylindrical, certain distortions and inaccuracies occur in a panoramic image created using many known technologies. In addition, image quality in many currently available systems is less than desired because, among other things, the panoramic images fail to provide an image in which the anterior front teeth, side teeth, sinus floor, and nerve canal appear clearly and in a manner that closely resembles the actual anatomy of the individual of whom the image is being taken. For example, some prior panoramic systems produce images with concaved front and hidden mandibular condyles.

Embodiments of the invention provide, among other things, a four-step process is used to generate an image having a more realistic depiction of actual anatomy than at least some prior-art devices. The first part of the process involves segmentation and visualization of the jaw (or bone) from other parts (flesh, gums, and the like) of the image. The first part of the process uses a "region growing algorithm." In a second part of the process, a detection of the jaw arch is carried out by separating image data into slices and applying a curve-fitting technique. In a third part of the process, information regarding the jaw arch is used to detect a master arch. Finally, in a fourth part of the process, a panoramic image is generated using the master arch and rendering geometry.

The invention also provides a method for generating a panoramic x-ray image. The method includes obtaining, with an x-ray detector, volumetric x-ray image data having a first plurality of slices, segmenting, with a computer, the x-ray image data into a first portion above a vertical threshold and a second portion below the vertical threshold, and separating the second portion into a second plurality of slices. The method further includes generating a plurality of curves for each slice in the second plurality of slices, generating a master arch for the second plurality of slices, and generating a panoramic image based on the master arch.

In addition, the invention provides a panoramic x-ray system with enhanced image quality. The system comprises a gantry, an x-ray source mounted on the gantry, an x-ray-detector mounted opposite the x-ray source on the gantry, and a computer that receives volumetric image data from the x-ray detector. The computer segments the image data into a first portion above a vertical threshold and a second portion below the vertical threshold, separates the second portion of data into a plurality of slices, generates a plurality of curves for each slice of the plurality of slices, generates a master arch for the plurality of slices, and generates a panoramic image based on the master arch.

The invention further provides a method of generating jaw image data. The method comprises obtaining, with an x-ray detector, volumetric x-ray image data including a plurality of slices, each slice having a plurality of voxel values. The method further comprises selecting, with a computer, a sagittal slice from the volumetric image data, and iteratively checking, with a computer, voxel values in the sagittal slice. The method further comprises seeding each slice in the plurality of slices, performing region growing, generating a set of images based on the region growing, and generating a three-dimensional image based on the set of images.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
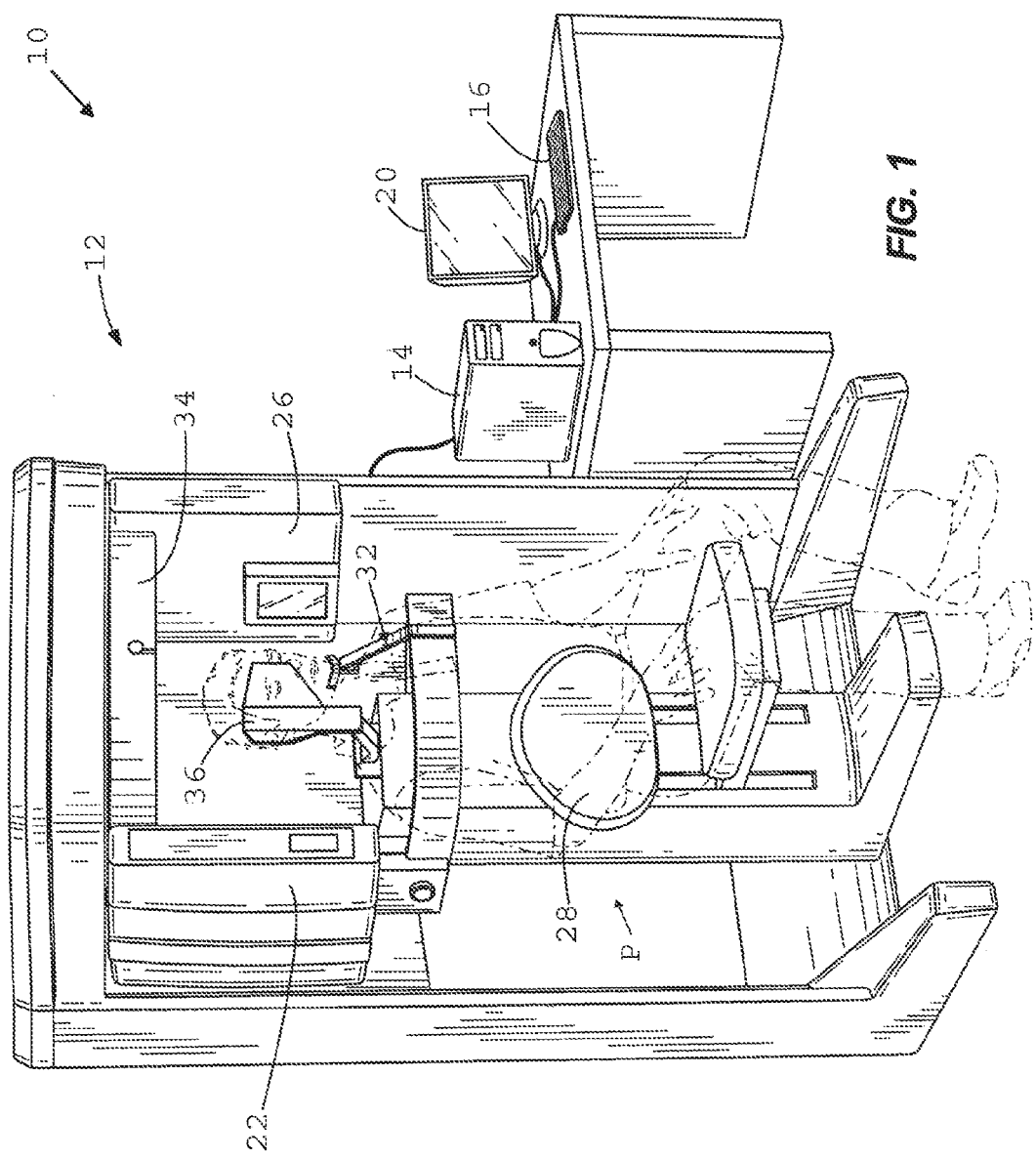
FIG. 1 is an illustration of a dental x-ray system for generating a panoramic x-ray image.

Referring to the drawings, and initially to FIG. 1, one form of a tomographic apparatus according to an embodiment of the invention, indicated generally by the reference numeral 10, includes a scanner 12 and a computer 14. The computer 14 has various input and output devices such as a keyboard 16, a cursor-control device (e.g., a mouse) and a monitor or display 20. The scanner 12 includes a source of x-rays 22, an x-ray detector or sensor 26, and a chair or seat 28. In the embodiment shown, the scanner 12 is arranged to image the head, or part of the head, of a human patient P, especially the jaws and teeth of the patient. The scanner also includes a rest or restrainer 32 to support the patient's head and face. The x-ray source 22 and sensor 26 are mounted on a rotating carrier or gantry 34 so as to circle round the patient's head, while remaining aligned with one another (opposite from one another). When the x-ray source is activated, it generates a stream of x-rays. When a patient is properly positioned in the seat 28 and restrainer 32, the x-rays (or at least some x-rays) pass through the patient's head and the sensor 26 generates x-ray images of the patient's head. Numerous images are generated as the source 22 and sensor 26 rotate around the patient's head. The computer 14 receives the x-ray image data from the scanner 12 and, as is discussed below, generates a panoramic image based on the captured image data.

As noted above, prior systems often produce panoramic images that are distorted or inaccurate. One objective of the invention is to provide a panoramic image that more accurately depicts the entire jaw denture structure, including the teeth, sinus floor, and mandibular condyles. Images generated using embodiments of the invention exhibit an anatomic structure size in a ratio of 1:1 that is uniformly proportional to the panoramic image from visualization and spatial-measurement perspectives.

Figure 2:
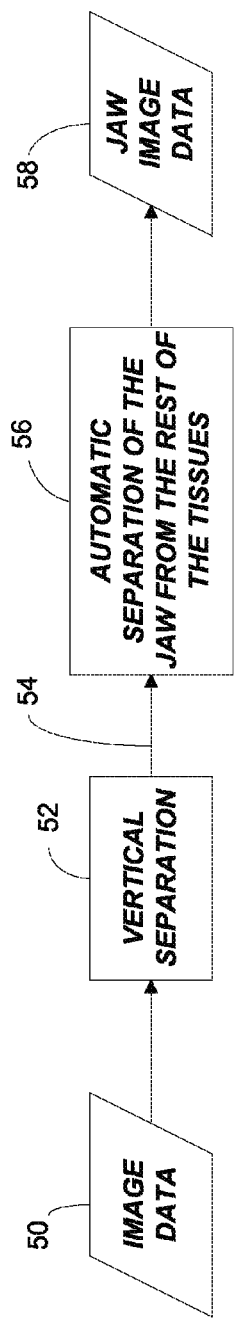
FIG. 2 is a flow chart illustrating a jaw segmentation and visualization process performed by the system shown in FIG. 1.
Figure 3:
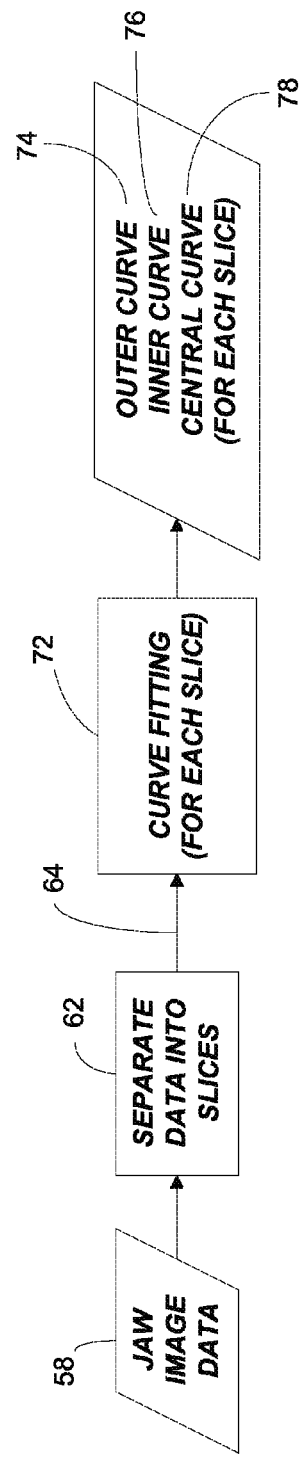
FIG. 3 is a flow chart illustrating an automatic jaw arch detection process performed by the system shown in FIG. 1.
Figure 4:
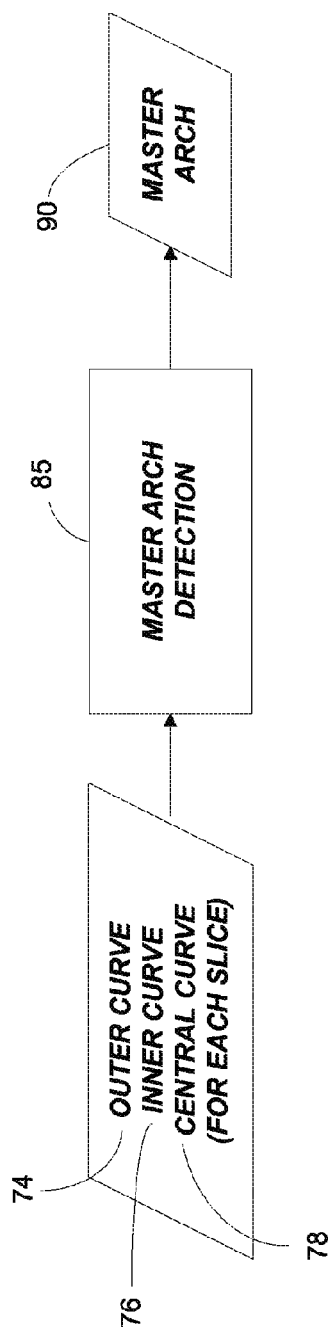
FIG. 4 is a flow chart illustrating a master arch detection process performed by the system shown in FIG. 1.
Figure 5:
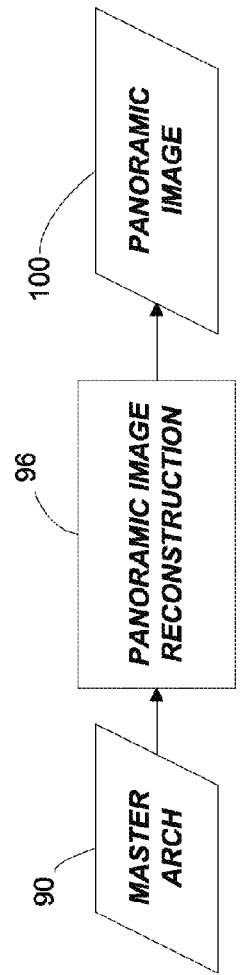
FIG. 5 is a flow chart illustrating a panoramic image reconstruction process performed by the system shown in FIG. 1.

FIGS. 2 through 5 show, in a general manner, an image generation process carried out by embodiments of the invention. The process is performed by the computer 14 based on image data, having plurality of slices, received from the scanner 12 (a volumetric x-ray image data set or a portion of a volumetric data set). Generally, the computer 14 is programmed with software designed to carry out the processes outlined below. It should be noted that embodiments of the invention could also be implemented using application-specific hardware or a combination of application-specific hardware and software running on programmable devices. As shown in FIG. 2, the first overall step in the process includes jaw segmentation and visualization. Image data 50 from the sensor 26 is processed by performing vertical separation (step 52) to separate or divide the image data into two portions: data below a vertical threshold and data above the vertical threshold. Divided data 54 (which includes data related to both soft tissue and hard tissue (e.g., bone)) is then processed (step 56) to separate soft tissue from hard tissue to produce jaw image data 58. As shown in FIG. 3, the jaw image data 58 is separated into slices 64 (step 62), and the slices 64 are modified using curve-fitting (step 72). The curve fitting generates three curves for each slice: an outer curve 74, inner curve 76, and central curve 78. These steps are performed by an automatic jaw arch detection process. As shown in FIG. 4, the curves 74-78 are used in a master arch detection process (step 85), which generates a master arch 90. As shown in FIG. 5, the master arch 90 is used in a panoramic image reconstruction process (step 96) to generate a panoramic image 100. Additional details of the process illustrated in FIGS. 2 through 5 are provided below.

Figure 6:
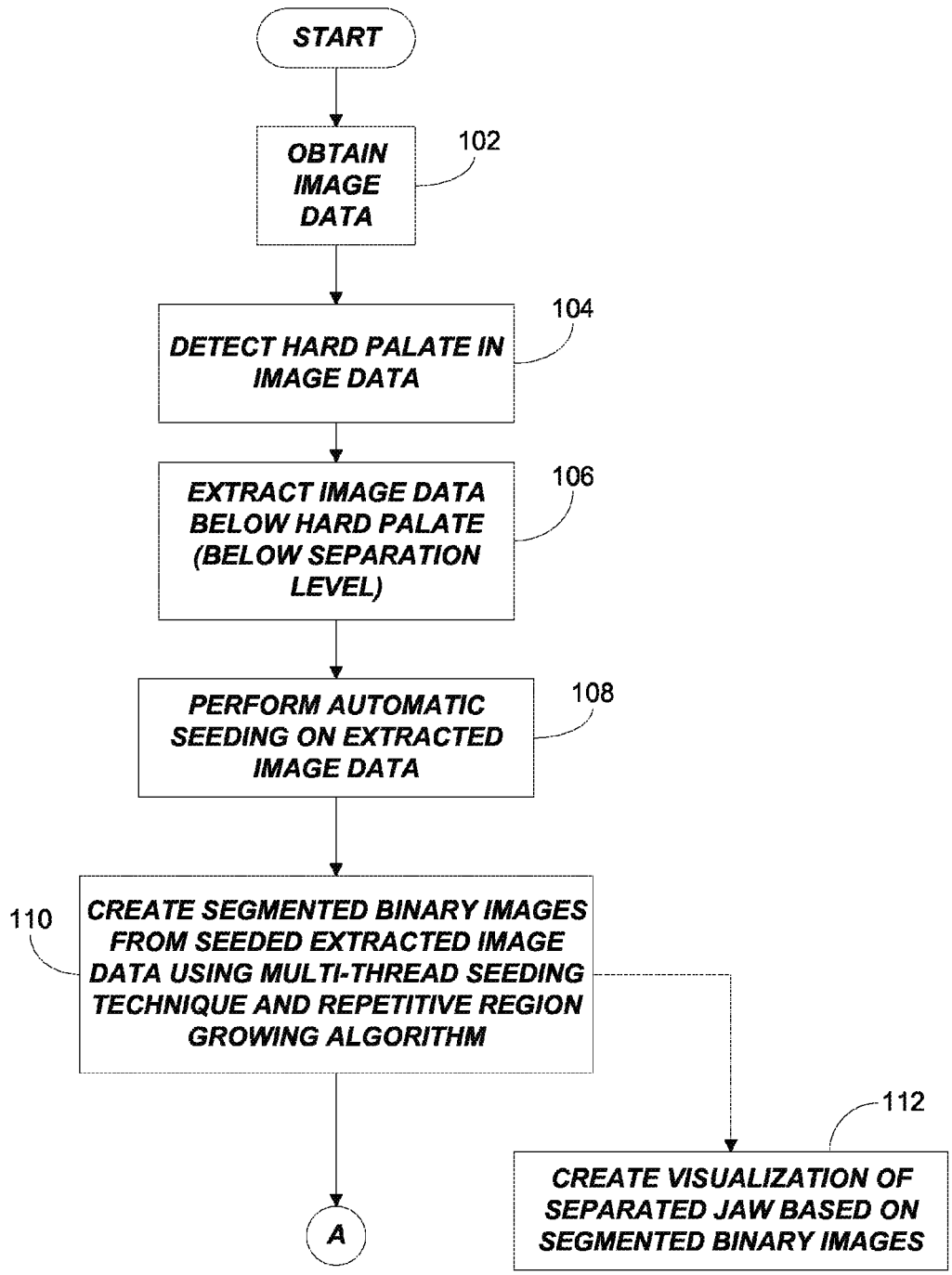
FIG. 6 is a flow chart illustrating the detail steps of the automatic jaw arch detection process of FIG. 2 in greater detail.

FIG. 6 provides additional information regarding the segmentation and visualization process of FIG. 2. As shown in FIG. 6, image data is obtained (step 102) (i.e., the image data 50) and segmentation is achieved by detecting the hard palate in the patient's jaw (step 104). The purpose of hard palate detection is to separate the anatomy of interest to a dentist (or other medical professional) from other parts of the head. Typically, the areas of interest include the mandible, mandibular condyles, maxilla, teeth, teeth apices, nerve canal paths, and sinus floor. Except for the mandibular condyles and sinus floor, the tissue and parts of the head located above the hard palate are typically not of interest to a dentist.

To detect the hard palate, the middle sagittal slice of image data is selected. Iterative checking of voxels in this slice of data is then used to determine the position of the hard palate (which is, of course, in general terms, an anatomical feature). The analysis of the data is impacted by a number of conditions including the presence of metal artifacts in the subject's teeth (e.g., fillings in cavities, braces, etc.), the upper space fosse, the lower hyoid, and the curvature of the hard palate.

In particular, the interactive voxel checking process checks voxel values starting from the right half of the middle sagittal slice. The check begins at the bottom of the sagittal slice and moves upward (in the vertical direction) and determines whether the voxel intensity values correspond to values associated with the hard palate or other anatomical features. A check is also performed to see if the values correspond to possible metal artifacts.

Once a voxel is determined (or verified) to be on the hard palate (understanding that that the hard palate is not a simple horizontal plane), a vertical level located a predetermined distance (e.g., 5 mm) below the vertical level of the verified voxel is selected as the separation level.

In a supplemental step, if the calculated value of the hard palate deviates from the average empirical value of the height of hard palate by more than a predetermined amount (e.g. few millimeters), a level below an empirical value of the hard palate (e.g., 5 mm below the empirical value) is selected as the separation level. In the particular embodiment described, the determined hard palate is used to divide or separate the anatomic features of interest from those portions of the head that are not of interest (step 106). Since most dental features are located below the hard palate, the output of this portion of the process is the dataset representing the image data below the separation level (or hard palate).

Once detection of the hard palate has occurred and the anatomy of interest has been separated from other anatomy (using the hard palate as a dividing line) (step 106), automatic seeding is performed as part of the overall process of separating the jaw (or bone) from soft tissue (step 108). (As should be understood, although the expression "separating bone from tissue" (or similar expressions) is (are) used, the image data is being separated or categorized as either data that represents bone or data that represents tissue.) The seeding is performed in a manner that accounts, at least in part, for challenges associated with distinguishing bone from tissue due to voids or gaps that may be present in or around the teeth. In addition, the seeding process also helps account for other areas of low density that may exist inside the mandible and maxilla (e.g., pockets of air or liquid).

To achieve segmentation where all or nearly all of the hard tissues or anatomical parts are separated from soft tissues (or parts), a multi-thread seeding technique is employed (step 110). The multi-thread seeding technique involves applying a two-dimensional grid net over the upper portion of each image slice. If an image point that overlaps with the grid net has an intensity higher than a predetermined amount (e.g., 900), the image point is selected as (or assumed to be) a bone point and put into the set of seeding points. The bone point selection process is performed from the top left to right across the image and moves from point to point with a predetermined gap (e.g., 3 mm). In one particular implementation, the total number of selected points is limited to a predetermined amount (e.g., 20).

Once bone points are selected, they are processed staring from the bottom slice that contains at least one bone point (i.e., a point with an intensity of a predetermined amount) and going up slice by slice (once a single bone point is found). If the last selected point on the current slice is far away from the last selected point (e.g., more than few millimeters) on the previous slice, then the selected points before the current slice are discarded (i.e., removed from the set of bone points) and the process restarts from the current slice. In this process, if no bone points are present in the current slice, the next slice is analyzed. Each image slice is processed until a predetermined height (e.g., a height no higher than the separation level (or hard palate)) is reached. After all the slices have been processed in one direction, the process is then reversed and performed in the opposite direction. Bone points detected or determined in the reverse direction are added to the set of seeding points. The number of the selected points for this downward or reverse process is also limited to a predetermined amount (e.g., 20). The total number of seeding points (i.e., bone points) is limited (e.g., 40) and forms an ordered set. To help achieve fast computation, an order of operations is obeyed in the region growing process (e.g., last in points are processed first).

Once the seeding is complete, a region growing segmentation process or algorithm is employed (step 110). The segmentation process determines whether the current point is a point on the jaw bone. If the point being evaluated (i.e., the current point) satisfies certain conditions, the point is classified as one to be included in the segmented volume.

After this classification, neighboring points on the same slice (e.g., 8 points (front, back, left, right, front-left, front-right, back-left, back-right)) and the two points above and below the current point are analyzed. The analysis performed is referred to as a "region growing process." Points within this set of 10 points that satisfy certain conditions are classified as seeding points. These conditions include modified intensity, standard deviation, and anatomical locations. The analysis of neighboring points is repeated for all of the seeding points.

As the process of classifying points in the segmented volume (i.e., the data representing the volume below the separation level or hard palate) occurs, the set of seeding points dynamically changes. In other words, the points in the set change during each cycle of the process because the points already classified in the segmented volume are not put into the set of seeding points again.

As should be apparent from the description above, the process of growing seeding points is a last-in, first-out process. Also, it is a local-nested process that fits the region with holes and gaps with multiple threads. The seeding process helps ensure that all isolated portions or bony portions with holes are evaluated or judged and, as appropriate, classified as bone or hard tissue.

The result or output of the multi-thread seeding and region growing process is a set of binary images. In one embodiment, "1s" in each image indicate voxels on the jaw and "0s" in the image indicate voxels off (or outside of) the jaw. As is described below in greater detail, the binary image data is processed further and ultimately used to produce a panoramic image. However, and as an alternative, the binary images can be used to render a three-dimensional image of the jaw separated from soft tissue (step 112) instead of or in addition to a panoramic image.

Figure 7:
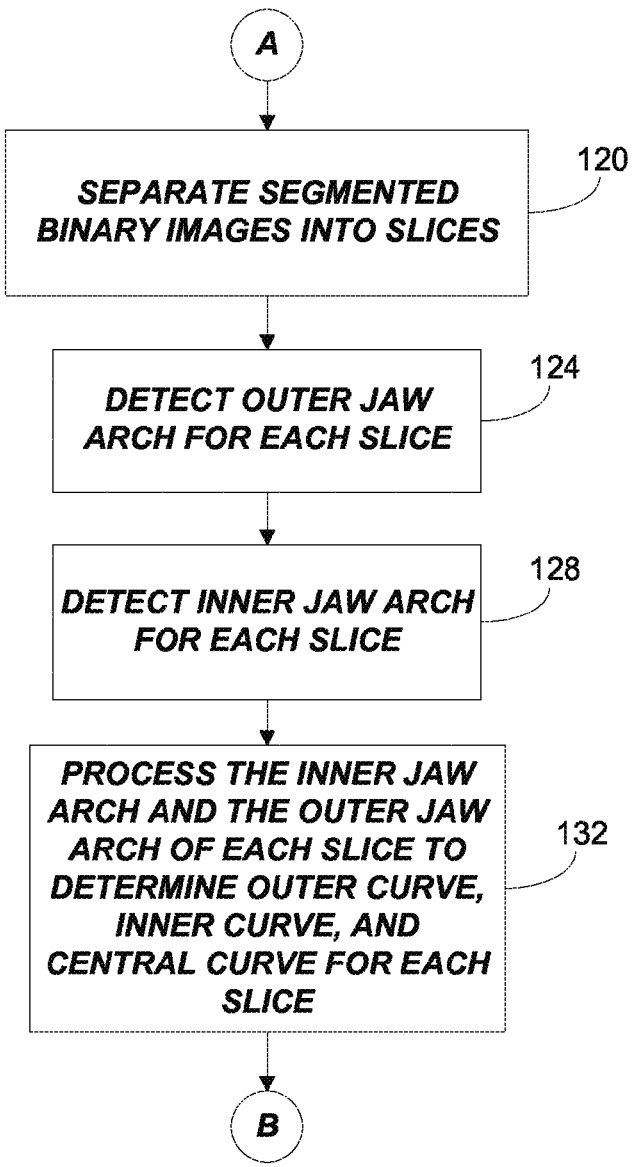
FIG. 7 is a flow chart illustrating the detail steps of the automatic jaw arch detection process of FIG. 3 in greater detail.

Once the binary images are produced, the binary image data is separated into slices, (step 120 of FIG. 7). This process involves putting the three-dimensionally segmented binary image data into a stack of binary, two-dimensional image slices. Performing this process helps speed computations that are performed in certain downstream steps.

After separating the binary image data into slices, an outer arch detection process is performed (step 124). In particular, the location of the outer arch in the segmented-volume, binary data is detected or determined. Outer arch detection is achieved by locating the envelope of the jaw in a two-dimensional slice from the outside of the jaw arch.

In one embodiment, two distance metrics are employed for outer arch boundary identification. One metric is the left distance from the left-most edge of the image to the nearest horizontal jaw bone, and the other metric is the right distance from the right-most edge of the image to the nearest horizontal jaw bone. Two parallel and combined procedures are performed for the left-half of the jaw arch and the right-half of the jaw arch. For the left-half of the jaw arch, the points with the local minimum distances and the points with smaller left distances than those immediately prior are considered boundary points. A similar process is applied to the right half of the jaw. The collection or set of these boundary points (i.e., the points from the left half and right half of the jaw) constitutes the outer boundary of the jaw arch. To achieve a better estimate of the jaw arch, a curvature-based interpolation of the set of boundary points is performed. More points are interpolated in regions with a high or relatively high curvature. The detected outer boundary points are ordered from small to large of their corresponding radial angles related to the left horizontal segment from the center of the image.

In addition to determining the location of the outer arch, the location of the inner arch is determined (step 128). In one embodiment, the inner arch boundary is detected by determining a fitting curve of the inner jaw arch in each two-dimensional slice from the inside of the jaw arch. In one embodiment, two distance metrics are employed for inner arch boundary identification. One metric is the left distance from a middle vertical line of the image to the nearest horizontal jaw bone, and the other metric is the right distance from a middle vertical line of the image to the nearest horizontal jaw bone. Two parallel and combined procedures are performed for the left-half of the jaw arch and the right-half of the jaw arch.

For the left-half of the jaw arch, the points with the local minimum distances and the points with smaller left distances than those points immediately prior are considered boundary points (referred to as the "inner arch boundary point rule.") A similar process is performed for (or boundary point rule is applied to) the right-half of the jaw arch. However, the inner arch boundary rule is valid only if the jaw has one concave shape at the very front region of the jaw. If the inner shape of the front jaw includes two concaves, the inner boundary points for each such concave are collected. Determining whether one or two concaves exist is accomplished by checking the voxels in the middle region of the line (or curve) for their locations and intensity. The collection of the above boundary points constitutes the inner boundary of the jaw arch.

As was done with the outer arch, to achieve a better estimate of the inner jaw arch, a curvature-based interpolation of the set of boundary points is performed. More points are interpolated in regions with a high or relatively high curvature. The detected outer boundary points are ordered from small to large of their corresponding radial angles related to the left horizontal segment from the center of the image.

As shown in step 132 of FIG. 7, the inner and outer boundaries of the jaw arch (or inner and outer arches) are processed so to produce an outer curve, inner curve, and central curve for each slice. The inner and outer boundaries are smoothed in three-dimensional shells formed by the boundaries themselves. The process helps eliminate scene discontinuity artifacts in the panoramic image (that is ultimately produced).

Boundary smoothing is performed in three-dimensions instead of in two-dimensions. A three-dimensional, spatial, lower-pass averaging filter is employed for the curve processing to obtain new points for both the inner boundary and the outer boundary. After smoothing of the inner and outer boundaries, the central curve of the jaw arch (normally called the location of the jaw arch) is obtained by averaging the inner boundary points and the outer boundary points with the same angles relative to the left horizontal segment from the center of the image. Points in pairs of points from the inner boundary and the outer boundary are arranged in a one-to-one ratio.

The smoothing process can also be referred to or characterized as a curve-fitting process, since the purpose is to make the inner and outer layers smooth enough to be seen as a natural surface of a real object, even though the curve is formed artificially based on the detected outer and inner curves.

Figure 8:
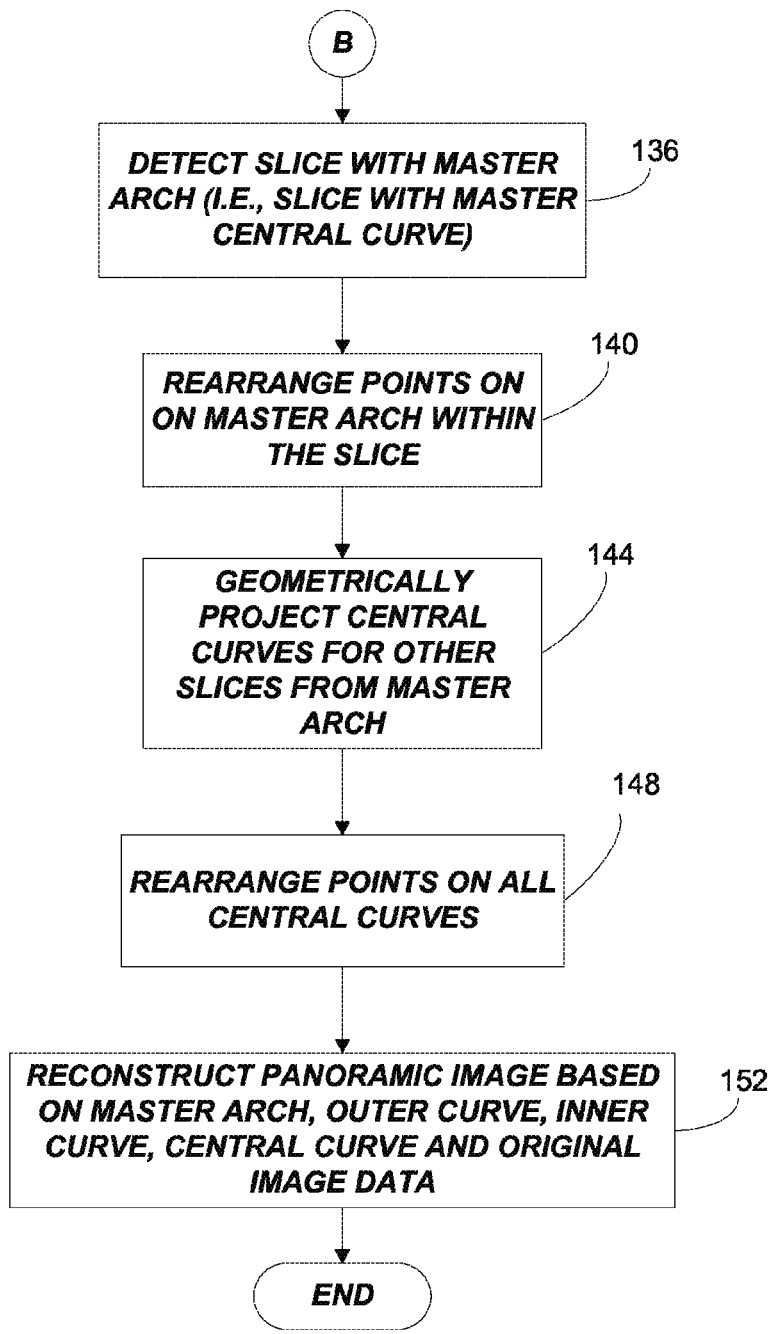
FIG. 8 is a flow chart illustrating the detail steps of the master arch detection process of FIG. 4 and the panoramic image reconstruction process of FIG. 5 in greater detail.

As shown in step 136 in FIG. 8, when the outer and inner arches have been detected and boundary smoothing performed, a master arch detection process is performed. One goal of the master arch detection process is to find an arch (central curve) on an axial slice which has the appearance of a solid shape. Preferably, the selected arch resembles a solid shape more than other axial arches in the slice of image data. Through observation and empirical investigation, it was determined that the slice containing a predetermined anatomical feature is the slice from which to determine the master arch. In particular, it has been determined that the slice containing the front portion of the cement-enamel junction ("CEJ") curve is the best slice from which to select the master arch. The master arch is roughly the longest curve in the slice and, generally, has relatively solid inner and outer boundaries that represent the typical shape of the jaw.

Determining the vertical level of the master arch from the chosen slice is accomplished by analyzing a local maximum protrusion of the front teeth. To find the local maximum front protrusion, a loop search of the front teeth data is performed to find the vertical level with the highest or largest level. If the vertical level of the master arch (i.e., the maximum protrusion) cannot be found using this procedure, a "golden" division (i.e., based on golden arithmetic) between the separation slice and the bottom slice containing the jaw bottom is performed to obtain the master arch level. Empirical testing has demonstrated that golden division works well for a database of more than 500 datasets.

After it is detected, the master arch is processed by rearranging the points on the master arch (step 140) so that it can be used for a uniformly-spaced projection (step 144). The projection is from the surface spanned by the master arch to all the central curves (i.e., the central curve in each slice).

Prior to making the projections, in step 140, the two tails of the master arch are processed so that they are positioned towards (or aligned with) the left and right boundaries of the master arch. The two tails are also extended until they touch the image boundaries. The extension helps ensure that the complete anatomies of all the other curves' tails (bounded by the master arch) are included (in the end image), because the curves in the teeth region may be longer than the non-extended master arch. The points on the master arch are counted to compute the length of the master arch. New evenly-spaced points are then generated and substituted for the previously existing points of the master arch. The number of new generated points for the master arch is equal to the length of the panoramic image to be produced. The distance between all of the neighboring points is one voxel wide.

Once the tails of the master arch are adjusted, orthogonal projections from the master arch are made (step 144). One projection is made to each central curve and the intersection points of the projected lines with the central curve are recorded or stored. If a projection does not cross a point on the central curve, the left closest point and the right closest point on the central curve are employed to create a point on the central curve. The relative distance of the left closest point to the projection and the relative distance of the right closest point to the projection are weighted in creation of a new point on the central curve. As a consequence, the number of the intersection points is the same as the number of points in the master arch. As noted above, this number is the length of the panoramic image to be reconstructed. The number of slices is the width of the panoramic image to be reconstructed.

The central curves are rearranged or reorganized using the new points generated through projection (step 148). The inner and outer arches, the central curves and the master arch are all used to create panoramic images (step 152). Two types of panoramic images can be produced at the user's discretion (e.g., based on user input indicating a desire for the system 10 to generate one type of image versus the other or both). The default one (referred to as a "radiograph") is similar to a conventional panoramic image. The other is referred to as a maximum intensity projection ("MIP") panoramic image.

Generating the radiograph involves finding the local normal vector at each point of the central curve. The direction of the normal vector is from the inside of the central curve to the outside of the central curve. Ray summation is performed along the normal vector from the inside to the outside to generate the default panoramic image. In one embodiment, the default path is 14 mm in length and with the point of the central curve as the center. Based on empirical evidence, this 14 mm thickness is a typical thickness of jaw arches. However, the thickness can be changed if the user desires.

For the MIP panoramic image, the maximum intensity is taken for the intensity of the panoramic image along the same path specified for the ray summation. For each point on the central curve, one pixel is identified and each central curve represents one horizontal line on the panoramic image. The slices form the entire panoramic image. However, the central curve on the separation slice is employed for all the slices above the separation level. The jaw anatomy above the separation level is nested with fosse and other tissue. Segmentation and inclusion of this bone information would create visual artifacts and hide the visualization of the sinus floor and mandibular condyles. Excluding this bone information increases the clarity of the sinus floor and mandibular condyles and yields a panoramic image that is similar or better than conventional radiographs.

Since the separation level (as well as the separation slice) is close to the teeth apices, the teeth apices and sinus floor region are pronounced and the continuity is naturally extended. Also, since the separation slice is far above the traditional focal trough, the comprehensive employment of the local bony information of the jaw below the separation slice makes the entire jaw more pronounced than traditional panoramic images and conventional radiographs.

Thus, the invention provides, among other things, an x-ray imaging system that generates improved panoramic images. Various features and advantages of the invention are set forth in the following claims.

What is claimed is:

1. A method of generating an image, the method comprising:
obtaining, with an x-ray detector, image data having a first plurality of slices;
defining a vertical threshold for the image data;
separating, with a computer, the image data into a first portion above the vertical threshold and a second portion below the vertical threshold;
processing, with the computer, the second portion to generate an arch; and
generating, with the computer, an image based on the arch.

2. The method as claimed in claim 1, wherein processing, with the computer, the second portion to generate an arch includes separating, with the computer, the second portion into a second plurality of slices; and
generating, with the computer, the arch for the second plurality of slices.

3. The method as claimed in claim 2, further comprising segmenting the second portion of the image data to separate image data that represents bone from image data that represents tissue.

4. The method as claimed in claim 3, further comprising performing a seeding process on an upper portion of each of the second plurality of slices.

5. The method as claimed in claim 4, wherein the seeding process includes a multi-thread seeding technique involving applying a two-dimensional grid net over the upper portion of each of the second plurality of slices.

6. The method as claimed in claim 2, wherein generating an arch for the plurality of slices includes generating a plurality of curves for each slice in the second plurality of slices.

7. The method as claimed in claim 6, wherein generating an arch for the plurality of slices includes determining a slice from the second plurality of slices that includes a predetermined anatomical feature and determining the longest curve in the slice.

8. The method as claimed in claim 6, wherein generating a plurality of curves for each slice in the second plurality of slices includes generating an outer curve, an inner curve, and a central curve.

9. The method as claimed in claim 1, further comprising making a plurality of projections from the arch.

10. The method as claimed in claim 1, further comprising; selecting a sagittal slice from the image data; and iteratively checking image element values in the sagittal slice.

11. An x-ray system comprising:
an x-ray source;
an x-ray detector positioned opposite the x-ray source; and
a computer that receives image data from the x-ray detector,
the computer defining a vertical threshold for the image data; separating the image data into a first portion above the vertical threshold and a second portion below the vertical threshold; separating the second portion of data into a plurality of slices; generating an arch for the plurality of slices; and generating an image based on the arch.

12. The system as claimed in claim 11, wherein the computer segments the second portion of the image data to separate image data that represents bone from image data that represents tissue.

13. The system as claimed in claim 12, wherein the computer performs a seeding process, over an upper portion of each slice.

14. The system as claimed in claim 13, wherein the seeding process includes a multi-thread seeding technique involving applying a two-dimensional grid net over the upper portion of each slice.

15. The system as claimed in claim 11, wherein generating an arch for the plurality of slices includes generating a plurality of curves for each slice of the plurality of slices, determining a slice from the plurality of slices that includes a predetermined anatomical feature, and determining the longest curve in the slice.

16. The system as claimed in claim 15, wherein generating a plurality of curves for each slice includes generating an outer curve, an inner curve, and a central curve.

17. The system as claimed in claim 11, wherein the computer generates a plurality of projections from the arch.

18. A method of generating an image, the method comprising:
obtaining, with an x-ray detector, image data including a plurality of slices, each slice having a plurality of voxel values;
selecting, with a computer, a predetermined slice from the image data;
iteratively checking, with the computer, voxel values in the predetermined slice;
seeding, with the computer, each slice in the plurality of slices;
generating, with the computer, a set of images based on region growing; and
generating a three-dimensional image based on the set of images.

* * * * *